(12) United States Patent
Baughman et al.

(10) Patent No.: US 10,386,190 B2
(45) Date of Patent: *Aug. 20, 2019

(54) COGNITIVE GUIDE SYSTEM FOR MULTI-OBJECTIVE EXCURSION

(71) Applicant: INTERNATIONAL BUSINESS MACHINES CORPORATION, Armonk, NY (US)

(72) Inventors: Aaron Keith Baughman, Silver Spring, MD (US); Christian Eggenberger, Zürich (CH); Lars Jenzer, Zürich (CH); Craig Matthew Trim, Sylmar, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,815

(22) Filed: Sep. 12, 2017

(65) Prior Publication Data

US 2018/0003509 A1 Jan. 4, 2018

Related U.S. Application Data

(63) Continuation of application No. 15/005,112, filed on Jan. 25, 2016, now Pat. No. 9,791,281.

(51) Int. Cl.
*A61B 5/00* (2006.01)
*A61B 5/01* (2006.01)
(Continued)

(52) U.S. Cl.
CPC .............. *G01C 21/20* (2013.01); *A61B 3/113* (2013.01); *A61B 5/0077* (2013.01); *A61B 5/01* (2013.01);
(Continued)

(58) Field of Classification Search
CPC ........... G01C 21/20; A61B 5/01; A61B 5/112; A61B 5/0077; A61B 3/113; A61B 7/04;
(Continued)

(56) References Cited

U.S. PATENT DOCUMENTS 6,759,972 B2 7/2004 Gupta et al.
9,471,059 B1 10/2016 Wilkins
(Continued)

FOREIGN PATENT DOCUMENTS

CN 202995797 U 6/2013
DE 102008059097 A1 5/2010
(Continued)

OTHER PUBLICATIONS

Katagiri et al., "An interactive multiobjective programming approach to tour route planning problems", Computational Intelligence & Applications (IWCIA), 2013 IEEE Sixth Intl. Workshop; Jul. 13, 2013; p. 167-171.
(Continued)

*Primary Examiner* — Michael J Zanelli
(74) *Attorney, Agent, or Firm* — Christopher McLane, Esq.; Hye Jin Lucy Song, Esq.; Heslin Rothenberg Farley & Mesiti, PC

(57) ABSTRACT

Methods, computer program products, and systems are presented. The methods include, for instance: providing a cognitive guide service to a group of participants for an excursion with an initial route planned by participants registration information and environment information along the initial route. During the excursion, real time sensory data on the participants and change in environment are collected by a cognitive agent accompanying the group to lead the excursion are relayed to a cognitive guide engine, and real time multi-objective optimization is modeled and performed. The participants are regrouped responsive to objectives of the excursion as represented by respective levels of interest in certain stage of the excursion as well as circumstances of the environment. Respective subgroups are formed from the participants per respective objectives, and respective new routes are selected from a set of optimal solutions for each subgroup. During the excursion, the cognitive guide engine iteratively optimizes routes responsive to incoming real time sensory data and objectives of the excursion.

20 Claims, 8 Drawing Sheets

(51) Int. Cl.
*A61B 5/11* (2006.01)
*A61B 7/04* (2006.01)
*G06N 5/02* (2006.01)
*A61B 3/113* (2006.01)
*G01C 21/20* (2006.01)
*G06Q 50/14* (2012.01)

(52) U.S. Cl.
CPC ............... *A61B 5/112* (2013.01); *A61B 7/04* (2013.01); *G06N 5/022* (2013.01); *G06Q 50/14* (2013.01); *B64C 2201/12* (2013.01)

(58) Field of Classification Search
CPC .... G06Q 50/14; G06Q 10/047; B64C 39/024; B64C 2201/12; G06N 5/022
See application file for complete search history.

(56) References Cited

U.S. PATENT DOCUMENTS

| | | |
|---|---|---|
| 2006/0265484 A1 | 11/2006 | Delia et al. |
| 2008/0145045 A1 | 6/2008 | Chen et al. |
| 2010/0030594 A1 | 2/2010 | Swart |
| 2012/0016585 A1 | 1/2012 | Muthuramalingam et al. |
| 2013/0038427 A1 | 2/2013 | Wang et al. |
| 2013/0332509 A1 | 12/2013 | Schwartz et al. |
| 2014/0022051 A1 | 1/2014 | Levien |
| 2014/0347973 A1 | 11/2014 | Yu et al. |
| 2015/0134143 A1 | 5/2015 | Willenborg |
| 2016/0340006 A1 | 11/2016 | Tang |
| 2017/0211940 A1 | 7/2017 | Baughman et al. |

FOREIGN PATENT DOCUMENTS

| | | |
|---|---|---|
| EP | 1221665 A1 | 7/2002 |
| WO | 2015028906 A1 | 3/2015 |

OTHER PUBLICATIONS

Mirk et al., "Virtual Tourism with Drones: Experiments and Lag Compensation", pp. 45-50 (ACM 2015).

"Multi-objective Optimization," https://en.wikipedia.org/wiki/Multi-objective_optimization (pp. 1-16; Sep. 2015).

Mell, Peter, et al., "The NIST Definition of Cloud Computing", NIST Special Publication 800-145, Sep. 2011, Gaithersburg, MD, 7 pgs.

Office Action in U.S. Appl. No. 15/005,112, dated Feb. 13, 2017, 31 pgs.

Notice of Allowance in U.S. Appl. No. 15/005,112, dated Jun. 8, 2017, 5 pgs.

List of IBM Patents or Applications Treated as Related, Sep. 12, 2017, pp. 1-2.

COGNITIVE GUIDE SYSTEM FOR MULTI-OBJECTIVE EXCURSION

TECHNICAL FIELD

The present disclosure relates to cognitive computing and multi-objective optimization, and more particularly to methods, computer program products, and systems for automated guide with real time adaptation.

BACKGROUND

Multi-objective optimization, also referred to as Pareto optimization, is an area of technology dealing with mathematical optimization problems having more than one objective function to be optimized simultaneously. In the areas where optimal decision taking trade-offs into account between multiple conflicting objectives are requested, such as areas of economics, logistics, and engineering, multi-objective optimization techniques are widely used. As multiple objectives are optimized, Pareto optimal solutions may be numerous for a problem.

Cognitive computing attempts to find best solutions in complex situations that are often ambiguous and uncertain, as in human problems, by computing contextual problem based on dynamic and shifting data collected in real time. Cognitive computing utilizes increasingly pervasive digital environment for data collection from people, high-speed processing, and wireless as well as mobile technologies.

SUMMARY

The shortcomings of the prior art are overcome, and additional advantages are provided, through the provision, in one aspect, of a method. The method includes, for example: collecting, by a cognitive guide engine running on a computer, sensory data on the participants and on environments of an excursion in real time captured by two or more cognitive agents accompanying and leading the group for the excursion with a present route such that the cognitive guide engine learns location of the group, respective pace of travel for the participants, and respective level of interest of the participants for a landmark in the present route; optimizing the present route by use of at least two objectives of the excursion in real time during the excursion, a first objective of the excursion from the at least two objectives being to minimize expenses for the excursion, and a second objective of the excursion from the at least two objectives being to maximize enjoyment of the participants, based on the collected real time sensory data; and notifying the participants and the two or more cognitive agents of two or more new routes in real time, responsive to the optimizing, respective new route of the two or more new routes corresponding to each subgroup of two or more subgroups, such that the participants continue the excursion with the respective new route.

The shortcomings of the prior art are overcome, and additional advantages are provided, through the provision, in one aspect, of a method. The method includes, for example: collecting, by a cognitive guide engine running on a computer, sensory data on the participants and on environments of an excursion in real time captured by two or more cognitive agents accompanying and leading the group for the excursion with a present route such that the cognitive guide engine learns location of the group, respective pace of travel for the participants, and respective level of interest of the participants for a landmark in the present route; optimizing, by the cognitive guide engine, the present route according to at least two objectives of the excursion in real time during the excursion, wherein each of the at least two objectives of the excursion is optimized based on the sensory data on the participants and on the environments of the excursion from the collecting in real time, and wherein the optimizing regroups the participants into subgroups respectively corresponding to each of the at least two objectives; and notifying, by the cognitive guide engine, two or more new routes that respectively correspond to the at least two objectives, to the participants of the subgroups and the two or more cognitive agents, such that the participants of the subgroups may respectively continue the excursion according to a respective new route that maximizes respective objectives of the at least two objectives optimized for each subgroup.

Additional features are realized through the techniques set forth herein. Other embodiments and aspects, including but not limited to computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
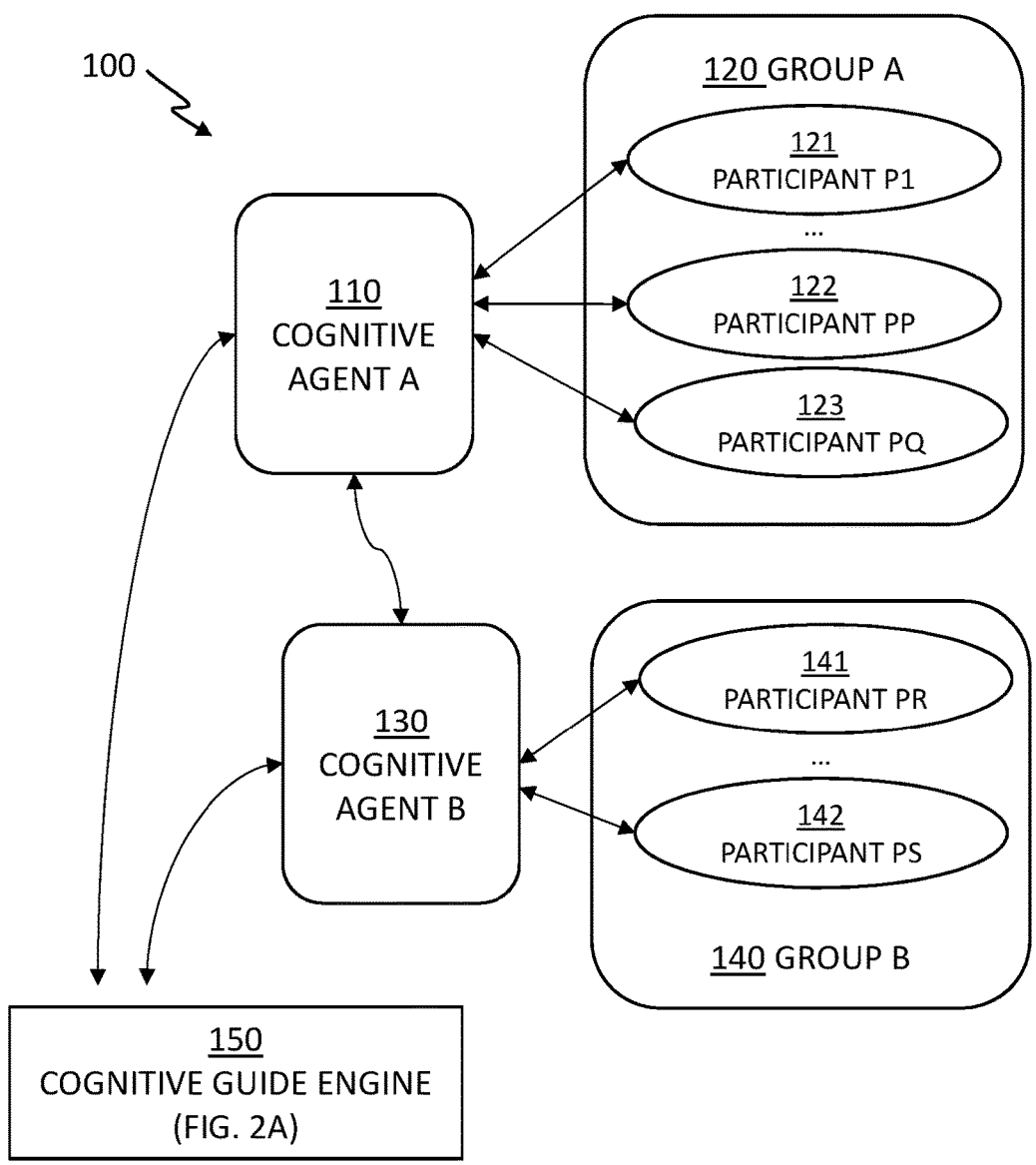
FIG. 1 depicts a cognitive guide system, in accordance with one or more aspects set forth herein.

FIG. 1 depicts a cognitive guide system 100, in accordance with one or more embodiments set forth herein.

The cognitive guide system 100 includes two or more cognitive agents, 110 and 130, and a cognitive guide engine 150, in order to guide an excursion for two or more participants, 121, 122, 123, 141, and 142, who are initially grouped into two or more groups, 120 and 140, according to various participants registration information useful for itinerary routing such as age and fitness level of the participants, 121, 122, 123, 141, and 142. The cognitive guide system 100 displays characteristics of cognitive computing as being adaptive to the changes in environment and the participants of the excursion, being interactive with participants by use of various mobile technologies, being iterative and stateful such that the cognitive guide system 100 accumulates data generated in the previous exchanges and applies accumulated data as the excursion progresses, and being contextual in gathering information from varied sources such that the cognitive guide system 100 continuously generates real time solutions based on a context encompassing wide variety of information.

In this embodiment, at the beginning of the excursion, the participants, 121, 122, 123, 141, and 142, are separated in two groups of group A 120 and group B 140. The group A 120 and the group B 140 may share an itinerary, in which case the participants in both the group A 120 and the group B 140 move as one group according to the same itinerary. The group A 120 includes a first participant P1 121, a p-th participant PP 122, and a q-th participant PQ 123 for the excursion. Similarly, the group B 140 includes an r-th participant PR 141, and s-th participant PS 142 for the same excursion serviced by the cognitive guide system 100 as the group A 120.

The cognitive agents include a cognitive agent A 110 and a cognitive agent B 130. The cognitive agent A 110 guides the group A 120 as well as collects real time sensory data being displayed by the participants, 121, 122, and 123, of the group A 120. Similarly, the cognitive agent B 130 guides the group B 140 as well as collects real time sensory data being displayed by the participants, 141 and 142, of the group B 140. The cognitive agents, 110 and 130, independently communicate with the cognitive guide engine 150, and communicate with each other to relay data or various other purposes. In one embodiment of the present invention, the cognitive agents are unmanned aerial vehicles (UAVs) equipped with capturing devices detecting the real time sensory data generated by the participants such as cameras, microphones, etc. In the same embodiment, the real time sensory data include, but are not limited to, visual, auditory, and gestural data generated by the participants. Examples of real time sensory data generated by the participants during the excursion include, but are not limited to, a pace of the excursion, gait, body temperature, eye movements, comment on certain spots of the excursion, interaction with other participants, etc., that may be interpreted as a level of interest in a specific spot in the excursion, physical condition, etc.

The cognitive agents 110 and 130 also relay data between mobile communication terminals belonging to a respective participants and the cognitive guide engine 150 such that the participants, 121, 122, 123, 141, and 142, are enabled to communicate with the cognitive guide engine 150 such that extra streaming data from a specific participant may be transmitted to the cognitive guide engine 150 and such that each participant may receive notification from the cognitive guide engine 150 of updates and/or new information on the excursion. In one embodiment of the present invention the mobile communication terminals may be, but are not limited to, a smartphone installed with a fitness applet capable of streaming fitness data including accelerometer readings to the cognitive guide engine 150 with permission from the participant.

The cognitive guide engine 150 iteratively computes optimal itineraries of all participants, 121, 122, 123, 141, and 142, of the excursion by use of multi-objective optimization, or Pareto optimization, and a statistical model for preferences as expressed by the participant. As a result, the cognitive guide engine 150 may reorganize the groups in the middle of the excursion, and reroute the reorganized groups based on the computed optimal itineraries. In computing the optimal itineraries, data collected during the excursion include, but are not limited to, the real time sensory data collected by the cognitive agents, other extra input provided by the participants, 121, 122, 123, 141, and 142, including streaming data from an individual mobile communication terminal of a participant, and preference feedback provided by each participant for itineraries. The cognitive guide engine may further utilize the registration information.

In one embodiment of the present invention, the optimal itineraries are Pareto solutions to a 2-objective optimization problem satisfying two conflicting objectives with minimal trade-offs. A first objective is to minimize the amount spent during the excursion for various entertainments such as entrance fee for a landmark during the excursion, etc. A second objective is to maximize enjoyment of the as experienced by the participants. See descriptions of FIGS. 2A, 2B, and 2C, for details.

Figure 2A:
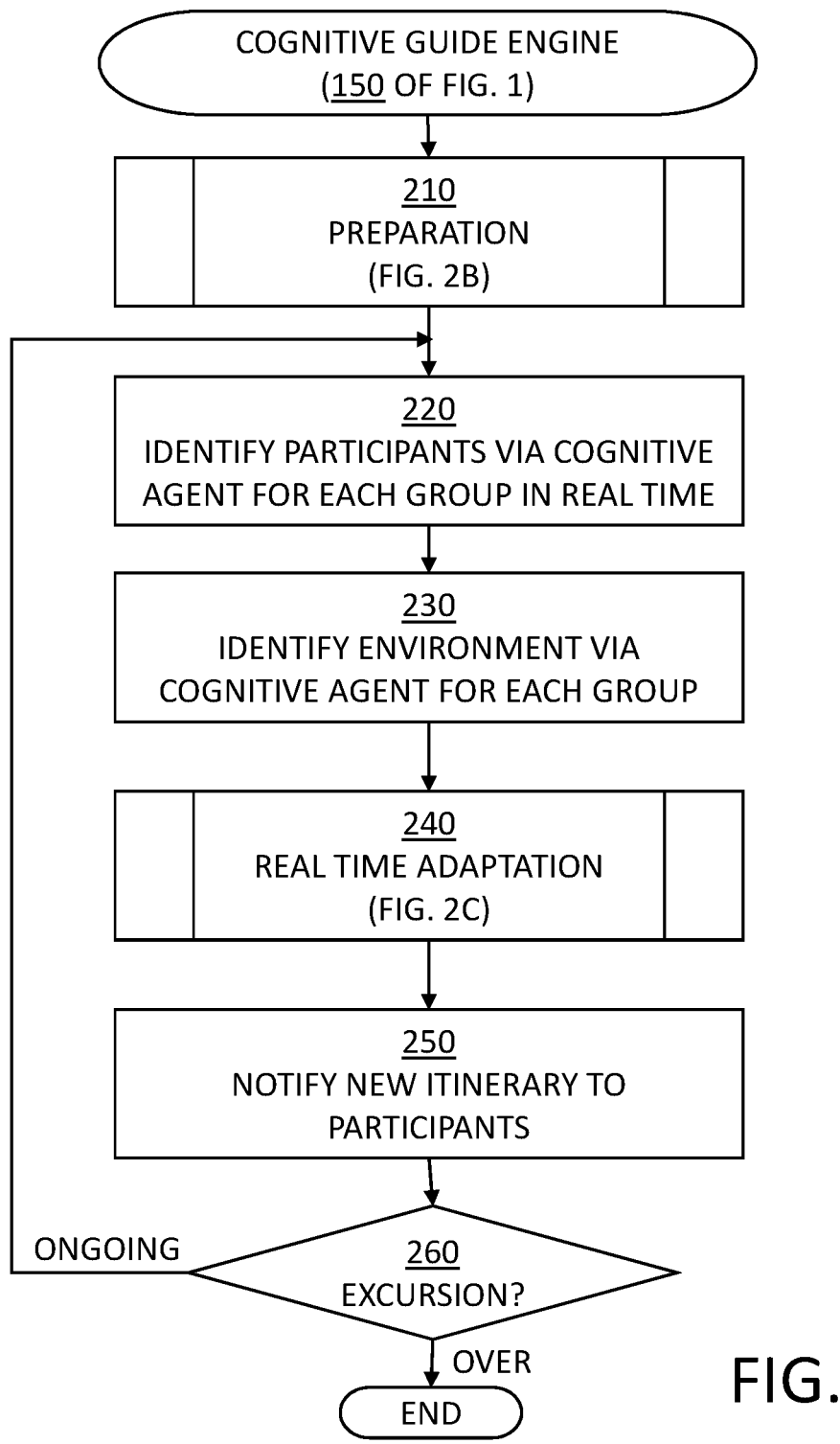
FIG. 2A depicts a flowchart for the cognitive guide engine of the cognitive guide system, in accordance with one or more embodiments set forth herein.

FIG. 2A depicts a flowchart for the cognitive guide engine 150 of the cognitive guide system 100, in accordance with one or more embodiments set forth herein.

In block 210, the cognitive guide engine 150 prepares the by registering participants prior to the excursion in preparation of the excursion. At the conclusion of block 210, the participants are grouped and an initial itinerary is set for each group based on the participant/environment information. See description of FIG. 2B for details. Then the cognitive guide engine proceeds with block 220.

In block 220, the cognitive guide engine 150 identifies, in real time, the participants by use of cognitive agents assigned for each group of participants. In one embodiment of the present invention, the participants may be identified by facial recognition using visual data collected by the cognitive agent. In other embodiment of the present invention, the participants may be identified by use of a radio-frequency identification (RFID) device. Then the cognitive guide engine proceeds with block 230.

In block 230, the cognitive guide engine 150 identifies, in real time, environment of the excursion by use of cognitive agents. Examples of the environment include, but are not limited to, the location of the groups by use of existing maps and/or real time topographical scanning data, weather at the time as collected from local weather information and/or weather data gathered through a temperature/wind/humidity sensors on the cognitive agents, obstacles, delays, emergencies, visitors in a specific landmark and/or traffic in the route of the excursion, etc. Then the cognitive guide engine proceeds with block 240.

In block 240, the cognitive guide engine 150 calculates real time optimal itineraries responsive to real time sensory data presented by the cognitive agents guiding the participants. See description of FIG. 2C for details. Then the cognitive guide engine proceeds with block 250.

In block 250, the cognitive guide engine 150 notifies a new itinerary calculated as a Pareto optimal from block 240 to the participants. Then the cognitive guide engine proceeds with block 260.

In block 260, the cognitive guide engine 150 determines whether or not the excursion is over. If the cognitive guide engine determines that the excursion is ongoing, then the cognitive guide engine loops back to block 220 to continue servicing the excursion by performing a next cycle of blocks 220, 230, 240, and 250. If the cognitive guide engine determines that the excursion is over, then the cognitive guide engine concludes servicing the excursion.

Figure 2B:
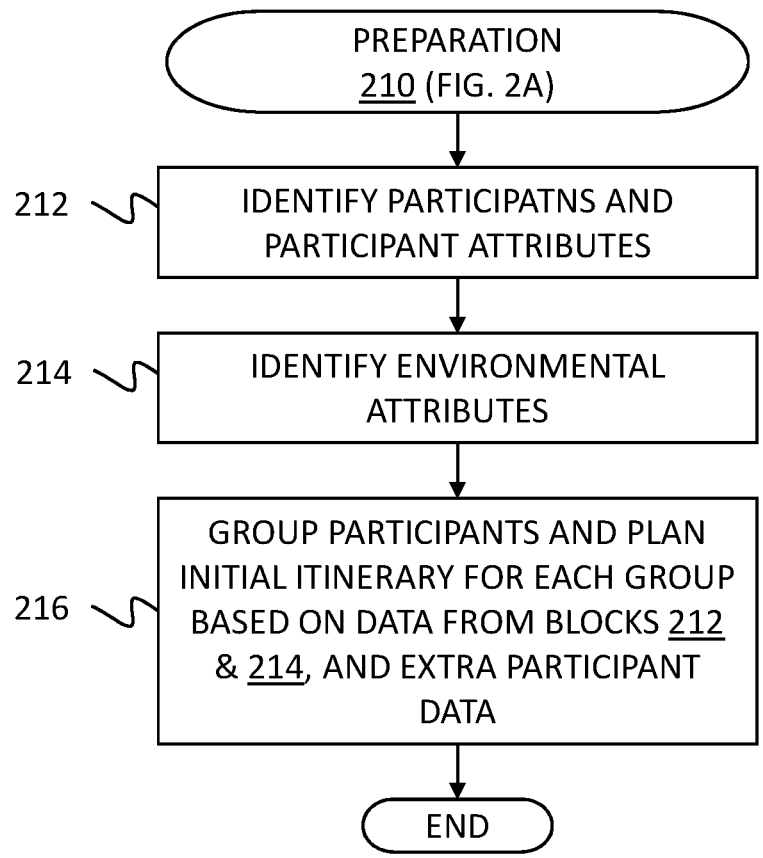
FIG. 2B depicts a flowchart for a preparation, as performed in block 210 of FIG. 2A by the cognitive guide engine, in accordance with one or more embodiments set forth herein.

FIG. 2B depicts a flowchart for a preparation, as performed in block 210 of FIG. 2A by the cognitive guide engine 150, in accordance with one or more embodiments set forth herein.

In block 212, the cognitive guide engine 150 identifies participants and attributes of respective participants before the excursion begins. Attributes may include, but are not limited to, facial features, estimated physical dimensions for seating arrangement in using various kind of vehicles, health characteristics such as comfortable pace and distance for walk, other health concerns for routing, and/or other information submitted for each participant upon registration. As noted, identification of respective participants may be made by use of visual facial recognition, and/or RFID device, etc. Then the cognitive guide engine proceeds with block 214.

In block 214, the cognitive guide engine 150 identifies environment of the excursion in preparation of the excursion, before the excursion begins. Examples of the environment include, but are not limited to, the location of the groups by use of existing maps and/or real time topographical scanning data by the cognitive agents guiding the excursion, weather for the period of the excursion as collected from local weather information and/or weather data gathered through a temperature/wind/humidity sensors on the cognitive agents, etc. Then the cognitive guide engine proceeds with block 216.

In block 216, the cognitive guide engine 150 groups the participants and produces an initial itinerary based on the participant information of block 212 and environment information of block 214. The participant information may further include a data stream made available by an individual mobile communication terminal for a specific participant, as transmitted by a fitness applet on a smartphone. Then the cognitive guide engine concludes the preparation and proceeds with block 220 of FIG. 2A.

Figure 2C:
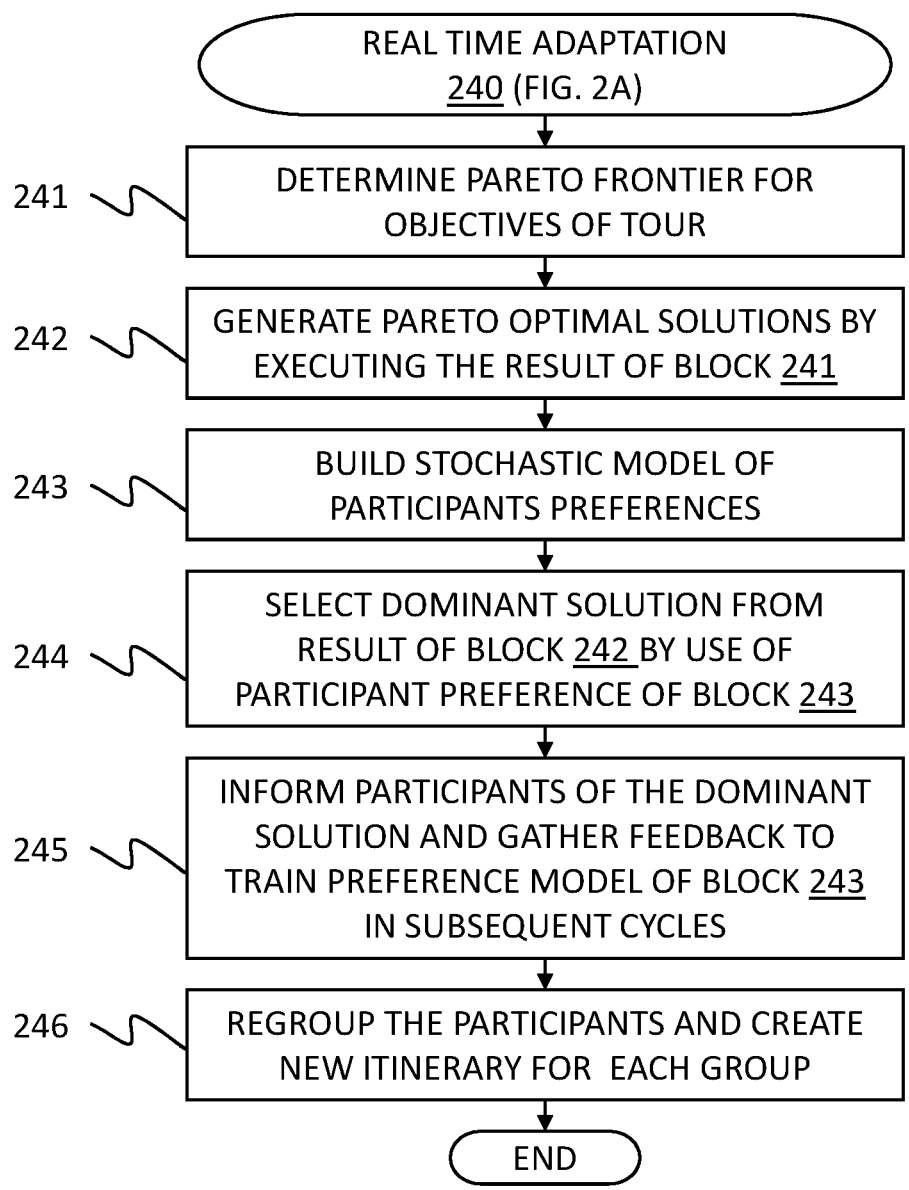
FIG. 2C depicts a flowchart for a real-time adaptation, as performed in block 240 of FIG. 2A by the cognitive guide engine, in accordance with one or more embodiments set forth herein.

FIG. 2C depicts a flowchart for a real-time adaptation, as performed in block 240 of FIG. 2A by the cognitive guide engine 150, in accordance with one or more embodiments set forth herein.

Terms Pareto optimal frontier, Pareto model, and dominant solution are used as defined in the context of multi-objective optimization in an area of multiple criteria decision making dealt by mathematical optimization. Pareto modeling and stochastic modeling are commonly done by mathematical optimization programming packages and will not be discussed in this specification.

In block 241, the cognitive guide engine 150 determines Pareto frontier that is a set of some solutions that are the most efficient within a certain dimensions, among all possible solutions. Pareto frontier may also be referred to as a Pareto model, for objectives of the excursion, specifying possibilities of various combinations of trade-offs amongst two objectives of the excursion, which are to minimize the expenses for the and to maximize enjoyment of the participants. Then the cognitive guide engine proceeds with block 242.

In block 242, the cognitive guide engine 150 executes the Pareto model determined in block 241. As a result, the cognitive guide engine generates a set of Pareto optimal solutions indicating a set of solutions optimally satisfying two conflicting objectives, among which neither of the two objectives can be improved in value without degrading the other objective values. The Pareto optimal solutions are also referred to as dominant solutions, nondominated solutions, Pareto efficient solutions, or noninferior solutions, etc. Then the cognitive guide engine proceeds with block 243.

In block 243, the cognitive guide engine 150 builds a stochastic model of participant preference. The stochastic model represents how probable an individual participant like or dislike a certain location visited during the excursion, based on feedback data provided by participants in the past and/or in the previous optimization cycles. Numerous Pareto optimal solutions resulting from block 242 are regarded as equally valuable, thus the stochastic model is employed to provide information on subjective preference on certain Pareto optimal solutions over other Pareto optimal solutions. For example, socially acceptable Pareto solutions may be sampled stochastically based on a percentage of people who prefer one solution to another. The percentage of preference later may be used to sample with a same distribution. Then the cognitive guide engine proceeds with block 244.

In block 244, the cognitive guide engine 150 selects a dominant solution from the set of Pareto optimal solutions. In one embodiment of the present invention, a tie-breaker determining a Pareto solution is the number of participants the Pareto solution may be applied to. Then the cognitive guide engine proceeds with block 245.

In block 245, the cognitive guide engine 150 informs the participants of the dominant solution and gathers feedback from participants on the dominant solution selected in block 244. The feedback may be immediately acquired by use of the cognitive agents, through facial expression, audio capture, etc. The cognitive guide engine utilizes the feedback to train the stochastic model of preference in a next real time adaptation cycle. Then the cognitive guide engine proceeds with block 246.

In block 246, the cognitive guide engine 150 regroup the participants and create a new itinerary for each group by use of the dominant solution selected in block 244. Then the cognitive guide engine concludes the real time adaptation and proceeds with block 250 of FIG. 2A.

Figure 3:
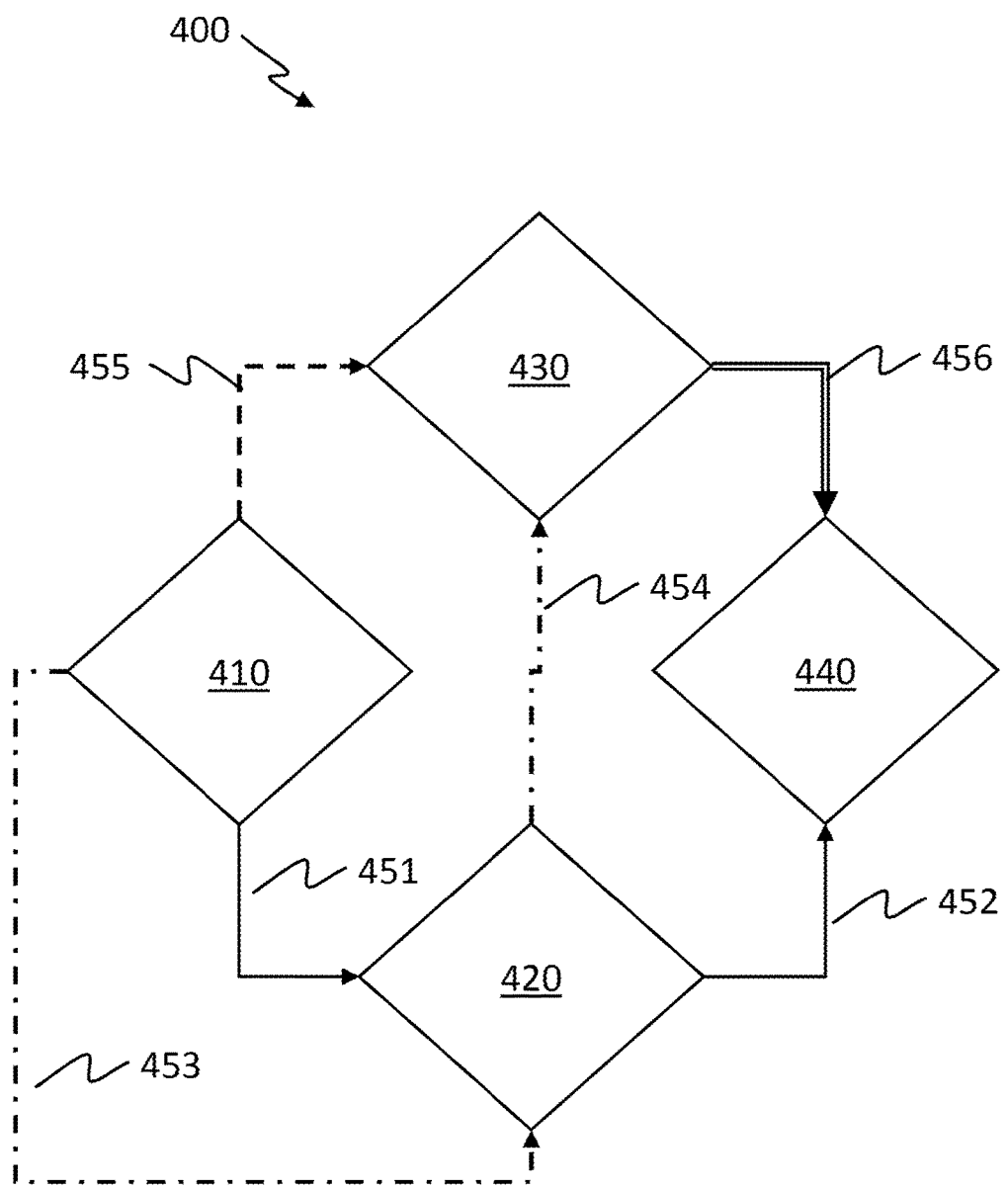
FIG. 3 depicts an exemplary itineraries as created by the cognitive guide engine, in accordance with one or more embodiments set forth herein.

FIG. 3 depicts an example of itineraries 400 as created by the cognitive guide engine, in accordance with one or more embodiments set forth herein.

An excursion through a city initially includes three (3) landmarks of a museum 410, a park 420, and a theater 440, for a group of twenty participants, using a shortest route represented in a first solid path 451 and a second solid path 452. The cognitive agents gather information that three participants in the group wish to spend more time in the museum 410 instead of moving on to the park 420, and the rest of the group wish to see as many places as possible. Accordingly, the cognitive guide engine 150 regroups the participants into a vanguard group of seventeen participants and a museum overstay group of three participants, and creates new itineraries respectively for each group.

For the museum overstay group of three, the cognitive guide engine 150 selects a new itinerary from the museum 410 to a monument 430, where the museum overstay group joins the vanguard group. The cognitive guide engine 150 directs a first cognitive agent, an unmanned aerial vehicle (UAV), to lead the museum overstay group from the museum 410 to the monument 430, via a dashed path 455, and to the theater 440, via a double-lined path 456.

For the vanguard group of seventeen, the cognitive guide engine 150 selects another new itinerary from the museum 410 to the park 420, and to the monument 430. From the museum 410 to the park 420, the cognitive guide engine 150 routes the vanguard group to travel via a first dash-dot path 453, which is longer than the first solid path 451 but passes through other landmarks, to make the detour interesting for the vanguard group and to create a delay for the museum overstay group. In rerouting, the cognitive guide engine 150 takes relative walking pace and interest level measured by the length of time spent on each landmark into account.

The cognitive guide engine 150 directs a second cognitive agent, another UAV, to lead the vanguard group from the museum 410 to the park 420, via the first dash-dot path 453, and to the monument 430, via a second dash-dot path 454, and to the theater 440, via the double-lined path 456.

The museum overstay group and the vanguard group travel from the monument 430 to the theater 440 via the double-lined path 456 either together or separately, completing their respective excursion approximately within a time frame similar to the original route of the excursion through the city including three landmarks.

Figure 4:
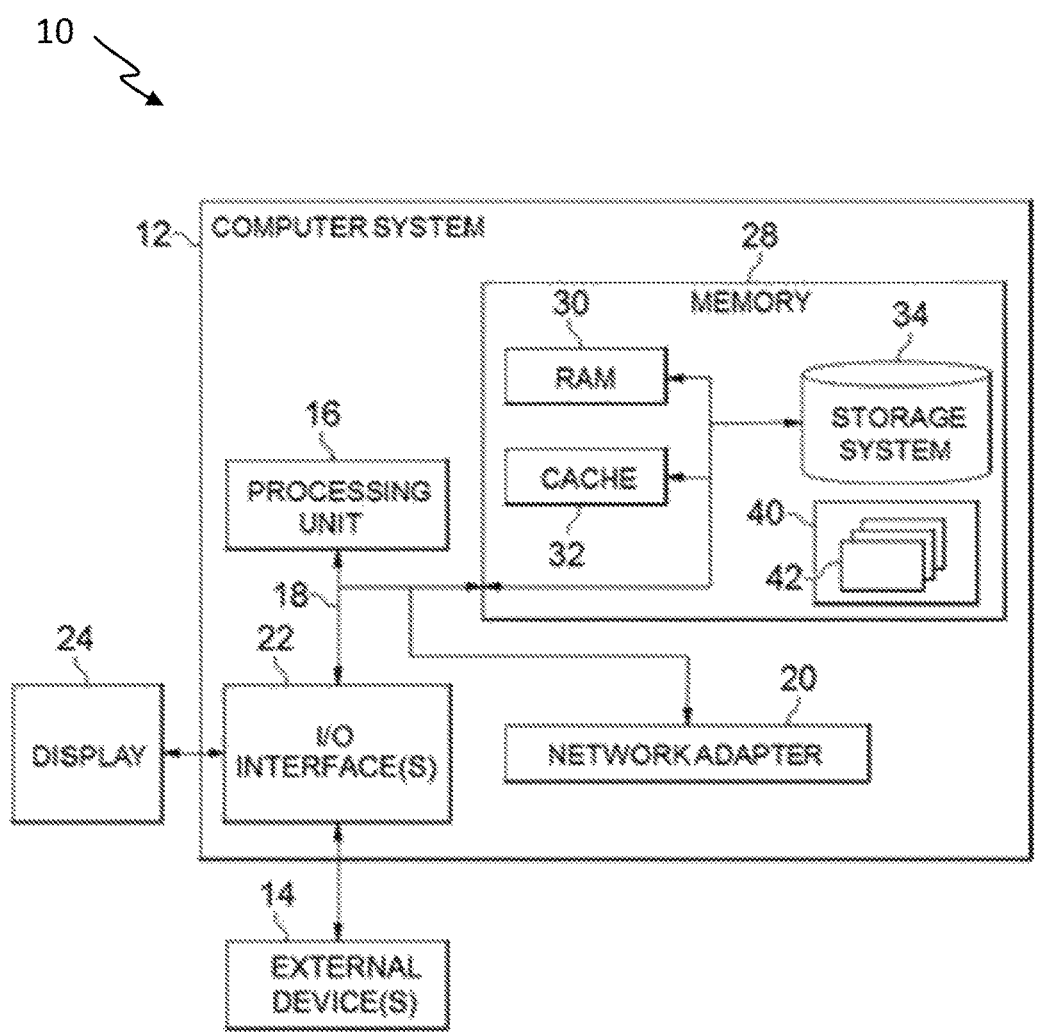
FIG. 4 depicts a cloud computing node according to an embodiment of the present invention.
Figure 5:
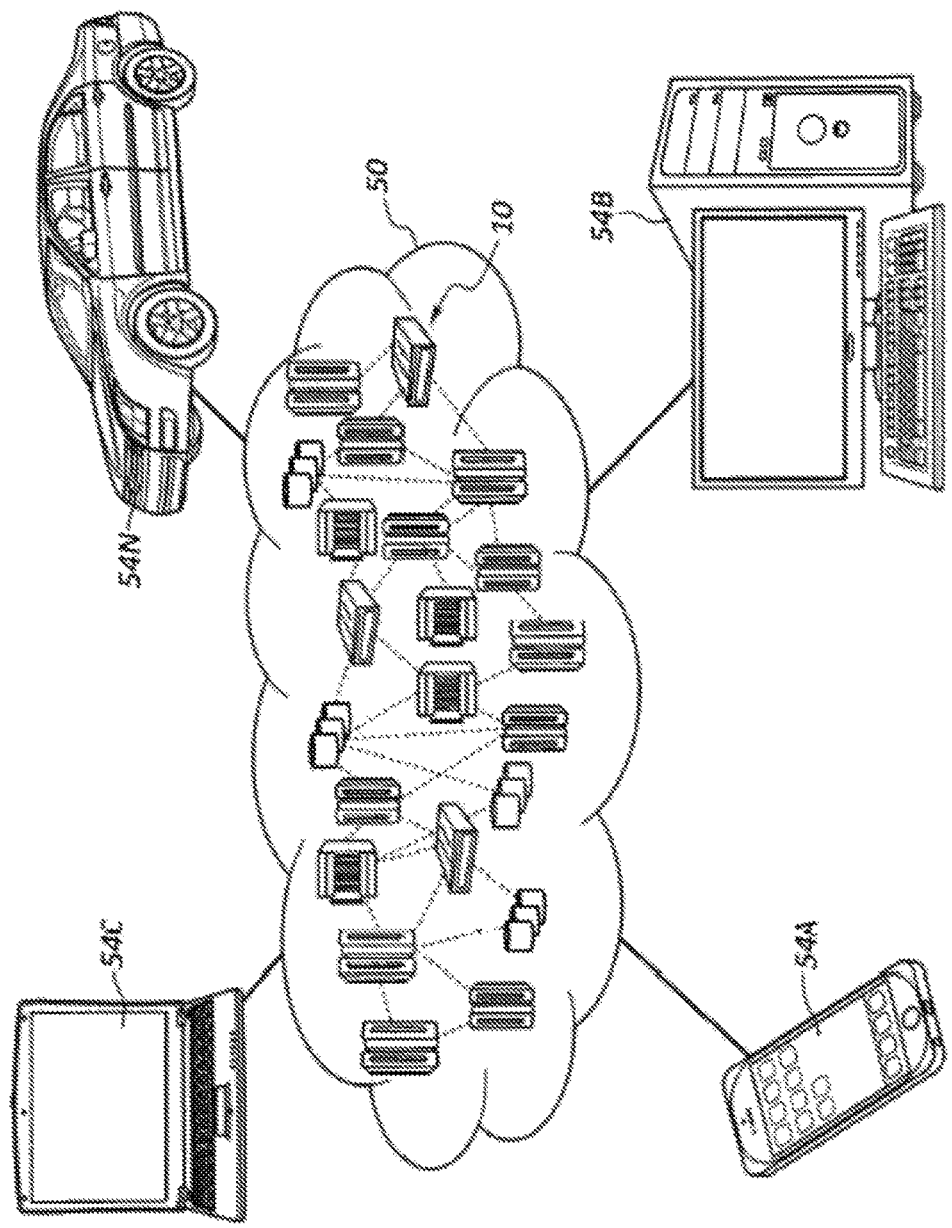
FIG. 5 depicts a cloud computing environment according to an embodiment of the present invention.
Figure 6:
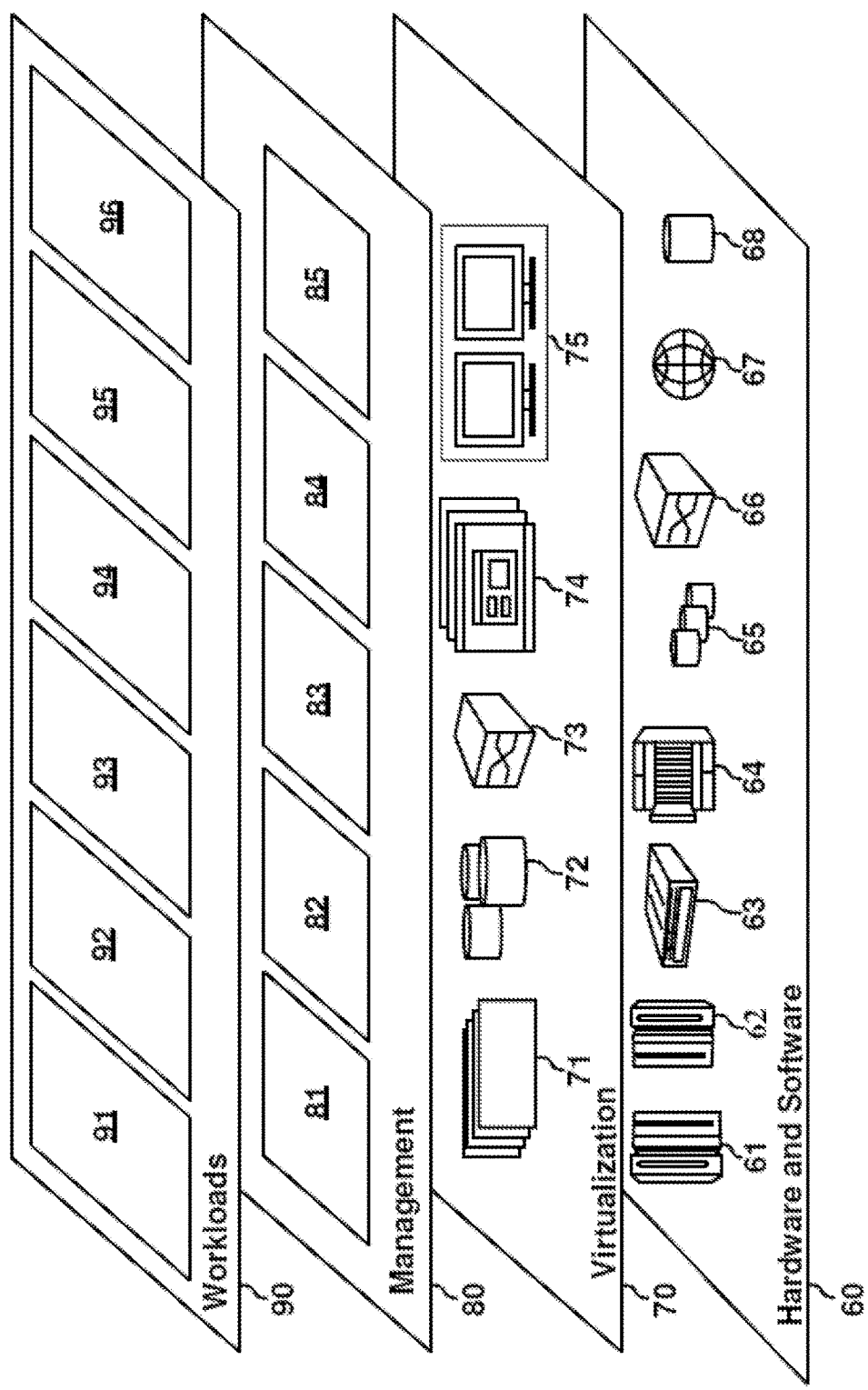
FIG. 6 depicts abstraction model layers according to an embodiment of the present invention.

FIGS. 4-6 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, a schematic of an example of a computer system/cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 12 in cloud computing node 10 is shown in the form of a general-purpose computing device. The components of computer system 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a cognitive guide system. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and various processing components of a cognitive guide system 96 as described herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method comprising:
    collecting, by a cognitive guide engine running on a computer, sensory data on the participants and on environments of an excursion in real time captured by two or more cognitive agents accompanying and leading the group for the excursion with a present route such that the cognitive guide engine learns location of the group, respective pace of travel for the participants, and respective level of interest of the participants for a landmark in the present route;
    optimizing, by the cognitive guide engine, the present route according to at least two objectives of the excursion in real time during the excursion, wherein each of the at least two objectives of the excursion is optimized based on the sensory data on the participants and on the environments of the excursion from the collecting in real time, and wherein the optimizing regroups the participants into subgroups respectively corresponding to each of the at least two objectives; and
    notifying, by the cognitive guide engine, two or more new routes that respectively correspond to the at least two objectives, to the participants of the subgroups and the two or more cognitive agents, such that the participants of the subgroups may respectively continue the excursion according to a respective new route that maximizes respective objectives of the at least two objectives optimized for each subgroup.

2. The computer implemented method of claim 1, said collecting comprising:
    obtaining the sensory data on the participants and on the environments of the excursion from a first cognitive agent of the two or more cognitive agents; and
    identifying a level of interest of a participant among the participants on the landmark by measuring time spent by the participant at the landmark.

3. The computer implemented method of claim 1, said optimizing comprising:
    determining a Pareto optimal frontier for the at least two objectives of the excursion, the Pareto optimal frontier specifying combinations of trade-offs between the at least two objectives;
    generating a set of Pareto optimal solutions satisfying the at least two objectives as much as possible with minimal trade-offs, by executing the determined Pareto optimal frontier;
    building a stochastic model of participant preference for the generated set of Pareto optimal solutions;
    selecting a dominant solution amongst the set of Pareto optimal solutions based on the stochastic model of participant preference;
    gathering feedback from the participants on the selected dominant solution upon informing the participants of the selected dominant solution to train the stochastic model of participant preference in subsequent cycles of the optimizing; and
    regrouping the participants into the two or more subgroups and creating the two or more new routes respectively for the two or more subgroups.

4. The computer implemented method of claim 1, further comprising:
    registering a first participant among the participants for the excursion with an initial route prior to the excursion, the initial route being calculated from individual participant registration data as provided by the first participant, the participant registration data including facial features for identification, estimated physical dimensions of the first participant for seating arrangement in vehicles, walking pace and distance comfortable for the first participant, as automatically determined by visual facial recognition, RFID, and combinations thereof.

5. The computer implemented method of claim 1, further comprising:
    leading a first subgroup of the two or more subgroups, by a first cognitive agent of the two or more cognitive agents, based on a first new route of the two or more new routes, responsive to the notifying.

6. The computer implemented method of claim 1,
wherein the two or more cognitive agents are respective unmanned aerial vehicles capable of real time sensory data collection and real time data communication,
wherein the sensory data comprises visual data, auditory data, and/or gestural data of the participants captured by respective devices installed on each cognitive agent,
wherein each cognitive agent of the two or more cognitive agents communicates in real time with the cognitive guide engine, other cognitive agents, and a mobile communication terminal of respective participants in the group, and
wherein said each cognitive agent relays data stream from the mobile communication terminal to the cognitive guide engine, the data stream being generated by an applet installed on the mobile communication terminal.

7. The computer implemented method of claim 1,
wherein the sensory data on the environment of the excursion comprises topographical scan of the present route, obstacles on the present route, weather, delays of the excursion caused by traffic, concentration of visitors in a landmark in the present route and/or an emergency to the participants, and
wherein the at least two objectives includes a first objective to minimize expenses for the excursion, and a second objective to maximize enjoyment of the participants on the excursion.

8. A computer program product comprising:
a computer readable storage medium readable by one or more processor and storing instructions for execution by the one or more processor for performing a method comprising:
collecting, by a cognitive guide engine running on the one or more processor, sensory data on the participants and on environments of an excursion in real time captured by two or more cognitive agents accompanying and leading the group for the excursion with a present route such that the cognitive guide engine learns location of the group, respective pace of travel for the participants, and respective level of interest of the participants for a landmark in the present route;
optimizing, by the cognitive guide engine, the present route according to at least two objectives of the excursion in real time during the excursion, wherein each of the at least two objectives of the excursion is optimized based on the sensory data on the participants and on the environments of the excursion from the collecting in real time, and wherein the optimizing regroups the participants into subgroups respectively corresponding to each of the at least two objectives; and
notifying, by the cognitive guide engine, two or more new routes that respectively correspond to the at least two objectives, to the participants of the subgroups and the two or more cognitive agents, such that the participants of the subgroups may respectively continue the excursion according to a respective new route that maximizes respective objectives of the at least two objectives optimized for each subgroup.

9. The computer program product of claim 8, said collecting comprising:
obtaining the sensory data on the participants and on the environments of the excursion from a first cognitive agent of the two or more cognitive agents; and
identifying a level of interest of a participant among the participants on the landmark by measuring time spent by the participant at the landmark.

10. The computer program product of claim 8, said optimizing comprising:
determining a Pareto optimal frontier for the at least two objectives of the excursion, the Pareto optimal frontier specifying combinations of trade-offs between the at least two objectives;
generating a set of Pareto optimal solutions satisfying the at least two objectives as much as possible with minimal trade-offs, by executing the determined Pareto optimal frontier;
building a stochastic model of participant preference for the generated set of Pareto optimal solutions;
selecting a dominant solution amongst the set of Pareto optimal solutions based on the stochastic model of participant preference;
gathering feedback from the participants on the selected dominant solution upon informing the participants of the selected dominant solution to train the stochastic model of participant preference in subsequent cycles of the optimizing; and
regrouping the participants into the two or more subgroups and creating the two or more new routes respectively for the two or more subgroups.

11. The computer program product of claim 8, further comprising:
registering a first participant among the participants for the excursion with an initial route prior to the excursion, the initial route being calculated from individual participant registration data as provided by the first participant, the participant registration data including facial features for identification, estimated physical dimensions of the first participant for seating arrangement in vehicles, walking pace and distance comfortable for the first participant, as automatically determined by visual facial recognition, RFID, and combinations thereof.

12. The computer program product of claim 8, further comprising:
leading a first subgroup of the two or more subgroups, by a first cognitive agent of the two or more cognitive agents, based on a first new route of the two or more new routes, responsive to the notifying.

13. The computer program product of claim 8,
wherein the two or more cognitive agents are respective unmanned aerial vehicles capable of real time sensory data collection and real time data communication,
wherein the sensory data comprises visual data, auditory data, and/or gestural data of the participants captured by respective devices installed on each cognitive agent,
wherein each cognitive agent of the two or more cognitive agents communicates in real time with the cognitive guide engine, other cognitive agents, and a mobile communication terminal of respective participants in the group, and
wherein said each cognitive agent relays data stream from the mobile communication terminal to the cognitive guide engine, the data stream being generated by an applet installed on the mobile communication terminal.

14. The computer program product of claim 8,
wherein the sensory data on the environment of the excursion comprises topographical scan of the present route, obstacles on the present route, weather, delays of the excursion caused by traffic, concentration of visitors in a landmark in the present route and/or an emergency to the participants, and wherein the at least two objectives includes a first objective to minimize expenses for the excursion, and a second objective to maximize enjoyment of the participants on the excursion.

15. A system comprising:
a memory;
one or more processor in communication with memory; and
program instructions executable by the one or more processor via the memory to perform a method comprising:
collecting, by a cognitive guide engine running on the one or more processor, sensory data on the participants and on environments of an excursion in real time captured by two or more cognitive agents accompanying and leading the group for the excursion with a present route such that the cognitive guide engine learns location of the group, respective pace of travel for the participants, and respective level of interest of the participants for a landmark in the present route;
optimizing, by the cognitive guide engine, the present route according to at least two objectives of the excursion in real time during the excursion, wherein each of the at least two objectives of the excursion is optimized based on the sensory data on the participants and on the environments of the excursion from the collecting in real time, and wherein the optimizing regroups the participants into subgroups respectively corresponding to each of the at least two objectives; and
notifying, by the cognitive guide engine, two or more new routes that respectively correspond to the at least two objectives, to the participants of the subgroups and the two or more cognitive agents, such that the participants of the subgroups may respectively continue the excursion according to a respective new route that maximizes respective objectives of the at least two objectives optimized for each subgroup.

16. The system of claim 15, said collecting comprising:
obtaining the sensory data on the participants and on the environments of the excursion from a first cognitive agent of the two or more cognitive agents; and
identifying a level of interest of a participant among the participants on the landmark by measuring time spent by the participant at the landmark.

17. The system of claim 15, said optimizing comprising:
determining a Pareto optimal frontier for the at least two objectives of the excursion, the Pareto optimal frontier specifying combinations of trade-offs between the at least two objectives;
generating a set of Pareto optimal solutions satisfying the at least two objectives as much as possible with minimal trade-offs, by executing the determined Pareto optimal frontier;
building a stochastic model of participant preference for the generated set of Pareto optimal solutions;

selecting a dominant solution amongst the set of Pareto optimal solutions based on the stochastic model of participant preference;
gathering feedback from the participants on the selected dominant solution upon informing the participants of the selected dominant solution to train the stochastic model of participant preference in subsequent cycles of the optimizing; and
regrouping the participants into the two or more subgroups and creating the two or more new routes respectively for the two or more subgroups.

18. The system of claim 15, further comprising:
registering a first participant among the participants for the excursion with an initial route prior to the excursion, the initial route being calculated from individual participant registration data as provided by the first participant, the participant registration data including facial features for identification, estimated physical dimensions of the first participant for seating arrangement in vehicles, walking pace and distance comfortable for the first participant, as automatically determined by visual facial recognition, RFID, and combinations thereof.

19. The system of claim 15, further comprising:
leading a first subgroup of the two or more subgroups, by a first cognitive agent of the two or more cognitive agents, based on a first new route of the two or more new routes, responsive to the notifying.

20. The system of claim 15,
wherein the two or more cognitive agents are respective unmanned aerial vehicles capable of real time sensory data collection and real time data communication,
wherein the sensory data comprises visual data, auditory data, and/or gestural data of the participants captured by respective devices installed on each cognitive agent,
wherein each cognitive agent of the two or more cognitive agents communicates in real time with the cognitive guide engine, other cognitive agents, and a mobile communication terminal of respective participants in the group,
wherein said each cognitive agent relays data stream from the mobile communication terminal to the cognitive guide engine, the data stream being generated by an applet installed on the mobile communication terminal,
wherein the sensory data on the environment of the excursion comprises topographical scan of the present route, obstacles on the present route, weather, delays of the excursion caused by traffic, concentration of visitors in a landmark in the present route and/or an emergency to the participants, and
wherein the at least two objectives includes a first objective to minimize expenses for the excursion, and a second objective to maximize enjoyment of the participants on the excursion.

* * * * *